United States Patent [19]
Shimamune et al.

[11] Patent Number: 4,818,572
[45] Date of Patent: Apr. 4, 1989

[54] PROCESS FOR PRODUCTION OF CALCIUM PHOSPHATE COMPOUND-COATED COMPOSITE MATERIAL

[75] Inventors: Takayuki Shimamune, Tokyo; Masashi Hosonuma, Kanagawa, both of Japan

[73] Assignee: Permelec Electrode Ltd., Kanagawa, Japan

[21] Appl. No.: 109,378

[22] Filed: Oct. 19, 1987

[30] Foreign Application Priority Data

Oct. 17, 1986 [JP] Japan ................. 61-247161
Oct. 17, 1986 [JP] Japan ................. 61-247162

[51] Int. Cl.$^4$ .................. B05D 3/00; B05D 3/2; C23C 22/08; C25D 5/00
[52] U.S. Cl. .................. 427/327; 204/38.1; 204/38.6; 204/140; 148/281; 148/286; 148/287
[58] Field of Search .................. 204/38.1, 38.6, 140; 427/327; 148/6.15 R; 428/469, 472.3

[56] References Cited

U.S. PATENT DOCUMENTS 3,451,871 6/1969 Bauer et al. ................. 204/140 X
4,108,690 8/1978 Heller ................. 148/6.15 R

FOREIGN PATENT DOCUMENTS 0071242 2/1983 European Pat. Off. .
0211676 8/1986 European Pat. Off. .
3709457 1/1987 Fed. Rep. of Germany .
2336913 12/1976 France .
2383656 3/1977 France .
 653709 3/1982 France .
1232944 5/1971 United Kingdom .

OTHER PUBLICATIONS

European Search Report.

*Primary Examiner*—Michael Lusignan
*Attorney, Agent, or Firm*—Sughrue, Mion, Zinn, Macpeak & Seas

[57] ABSTRACT

A process for production of a calcium phosphate compound-coated composite material is disclosed, comprising oxidizing a metallic substrate to form a layer of the oxide of the metal component of the metallic substrate on the surface thereof, and forming a coating layer of a calcium phosphate compound on the surface of the oxide layer.

11 Claims, No Drawings

PROCESS FOR PRODUCTION OF CALCIUM PHOSPHATE COMPOUND-COATED COMPOSITE MATERIAL

FIELD OF THE INVENTION

The present invention relates to a process for producing a composite material comprising a metallic substrate covered with a calcium phosphate compound which is excellent in affinity to the tissue of bone or teeth and thus which is useful as an implant material such as artificial bone, tooth and tooth root, or as a bonding material for such implant materials.

BACKGROUND OF THE INVENTION

A living body implant material such as artificial bone and artificial tooth root(s) has been receiving great attention in recent years because when the bone is broken and lost by an accident, for example, or the tooth is taken out, it can be restored by bonding the implant material or planting the implant material in the jaw bone, and thus the bone or tooth can be used in the nearly original form and a comfortable life can be enjoyed. Since, however, the implant material is embedded in the living body, it is essential that the material be harmless to the human body and must satisfy such requirements as having sufficiently high strength, good processability no dissolution, suitable specific density and good affinity to the living body.

Metals such as noble metals, alloys such as stainless steel, ceramics such as α-alumina, and in addition, apatite have heretofore been used as the implant material. These materials, however, have at least one of such disadvantages that toxicity is exhibited, strength is insufficiently low, processability is poor, dissolution occurs, and affinity to the living body is poor.

In order to eliminate the above disadvantage, it has been desired to develop metals or ceramics which, when apatite is coated on the surface thereof, provide a composite material having good affinity to the living body. For this purpose, a technique to bond metal and ceramic, or to bond ceramic and ceramic is needed. As such a metal-ceramic bonding technique or ceramic-ceramic bonding technique, only a plasma spray coating method has been known. This plasma spray coating method, however, has disadvantages in that the yield of expensive apatite particles is low and the bonding between the coating and the substrate is not always sufficiently high. Moreover, if the plasma spray coating method is applied under too severe conditions, partial decomposition occurs during the spray coating process and it becomes necessary to apply additional treatments such as crystallization.

In order to overcome the above prior art problems, the present inventors with another person have proposed an implant material in which a metallic substrate and a coating of a calcium phosphate compound are firmly bonded with an intermediate layer containing calcium phosphate compound sandwiched therebetween (Japanese Patent Application Nos. 64012/86, 64013/86 and 70504/86, corresponding. to U.S. patent application Ser. No. 29,519 filed Mar. 24, 1987), and an implant material in which a metallic substrate and a coating of calcium phosphate are bonded together with no intermediate layer sandwiched therebetween (Japanese Patent Application No. 169547/86, corresponding to U.S. patent application Ser. No. 74,837 filed July 17, 1987), and moreover all can be produced without the use of the spray coating method.

In these implant materials, the bonding strength between the metallic substrate and .the coating of the calcium phosphate compound is sufficiently high. However, when they are embedded in the living body, the coating of the calcium phosphate compound having good affinity to the bone tissue may assimilate with the bond tissue, finally bringing the metallic substrate in direct contact with the bond tissue. Since the affinity of the metallic substrate to the bone tissue is poor, the bone tissue regresses, thereby degrading the bonding between the bone tissue and the metallic substrate, and in the worst case, the implant material may be rejected.

SUMMARY OF THE INVENTION

An object of the present invention is to provide a process for production of a composite material which is good in workability, is of sufficiently high mechanical strength, has increased affinity to the bone tissue, and can maintain stable bonding properties over a long time, and thus which is suitable as an implant material such as an artificial bone and an artificial tooth root.

The present invention relates to a process for producing a calcium phosphate compound-coated composite material which comprises oxidizing a metallic substrate either by heating or electrolytically to form a layer of the oxide of the metallic substrate component alone or a layer of a mixed oxide of the metallic substrate component and a metal component in the electrolyte; if desired, heating the metallic substrate to stabilize the surface thereof; and then forming a coating of a calcium phosphate compound on the surface thereof.

The major feature of the present invention resides in that the oxide layer or mixed oxide layer of metal oxide or metal oxides, having relatively good affinity in the living body and having sufficiently high corrosion resistance is formed between the metallic substrate and the calcium phosphate compound coating by oxidizing either by heating or electrolytically, and in that the oxide or mixed oxide layer, even when the calcium phosphate compound coating is absorbed in the bone tissue, prevents the metallic substrate from coming in direct contact with the bone tissue and the thus prevents degradation of the bonding properties between the metallic substrate and the bone tissue.

DETAILED DESCRIPTION OF THE INVENTION

The first embodiment of the present invention relates to a process for producing a calcium phosphate compound-coated composite material suitable as an implant material which comprises heat-oxidizing a metallic substrate to form on the surface of the metallic substrate a layer of the oxide of the metallic substrate component which is excellent in corrosion resistance in the living body, and then forming a coating of a calcium phosphate compound such as apatite hydroxide excellent in affinity to the living body on the surface of the above oxide layer.

The second embodiment of the present invention relates to a process for producing a calcium phosphate compound-coated composite material suitable as an implant material which comprises electrolyzing a metallic substrate in an electrolyte to form on the surface thereof a coating of the oxide of the metallic substrate component alone or of a mixed oxide of the metallic substrate component and a metal component of the electrolyte, which is excellent in corrosion resistance in the living body, and then forming a coating of a calcium phosphate compound such as apatite hydroxide having excellent affinity to the living body on the surface of the above oxide or mixed oxide layer.

In accordance with the present invention, there can be obtained a composite material which can be bonded to the bone tissue, for example, in the living body with a sufficiently large affinity force, can hold a stable affinity force over a long time, and which does not exert adverse influences in the living body.

The metallic substrate as used herein means a substrate made of metal selected from titanium, titanium alloys, stainless steel, a chromium-cobalt alloy and so forth which are stable in the living body. The titanium and titanium alloys include metallic titanium and titanium alloys of titanium and Ta, Nb, platinum group metals, Al, V and so forth. The stainless steel as used herein includes JIS (Japanese Industry Standards) SUS 304, 310 and 316. The cobalt-chromium alloy as used herein includes corrosion resistant alloys such as a cobalt-chromium alloy for embedding in the living body. The metallic substrate made of the metal as described above may be in a form of, e.g., a plate and a bar, may be smooth on the surface, may have a porous surface like a sponge, or may be an expanded mesh or porous plate. The reason why the metals as described above are used as the substrate is that the metals have a sufficiently high mechanical strength and can be easily molded in comparison with sintered materials and glass.

The surface of the metallic substrate may be previously subjected to a rinsing treatment such as washing with water, acid, supersonic waves, steam and so on, to remove impurities thereon and increase the uniformity of the oxide or mixed oxide layer formed by electrolysis. In addition, if desired, the surface of the metallic substrate may be made coarse by applying a blast and/or etching treatment to increase the affinity to the calcium phosphate compound layer as described hereinafter and at the same time, to conduct activation. The above etching includes, as well as chemical etching, physical etching such as sputtering.

Then the metallic substrate is oxidized thermally or electrolytically to form an oxide or mixed oxide layer on the surface thereof.

In the first embodiment of the invention, the surface of the metallic substrate is heat-oxidized to form a layer of the oxide of the metal component of the metallic substrate. On heating the metallic substrate in an oxidizing atmosphere such as air to about 400° to 1,000° C., the oxide layer is formed in a thickness depending on the type of the metallic substrate. In the case of a substrate having relatively high thermal resistance, as one made of titanium, a titanium alloy, stainless steel or a chromium-cobalt alloy, the thickness of the oxide layer is as relatively thin as about several ten to several hundred angstromes (Å). Even with this thickness, the object of the present invention can be attained. In some cases, it is preferred to form an oxide layer having a larger thickness. In this case, if necessary, acid treatment as described hereinafter can be applied or a metal hydride compound can be formed.

For the acid treatment, it suffices that the metallic substrate be treated with a solution containing a corrosive inorganic or organic acid such as hydrochloric acid, sulfuric acid, nitric acid and oxalic acid by techniques such as the coating method and the soaking method. Thereafter, the oxide layer is formed by heating to about 300° to 800° C. As a result of the acid treatment, the surface of the metallic substrate prior to heating is corroded, and the effect of the heating reaches deeper portions of the inside of the layer, thereby forming an oxide layer having a larger thickness. For example, in the case of titanium or a titanium alloy, if the substrate is heated without application of the acid treatment, a yellow oxide is formed. On the other hand, if the substrate is heated after the acid treatment, a blue oxide layer having a relatively large thickness is formed and even after the formation of the oxide, the surface remains in the corrosion state, i.e., coarsened state and, therefore, it becomes possible to form more firmly the calcium phosphate compound coating layer. Also in the case of stainless steel, a chromium-cobalt alloy or other metals, like in the case of titanium and titanium alloys, a thick and stable oxide layer can be formed at lower temperatures.

In the case where the metallic substrate is made of stainless steel or a chromium-cobalt alloy, if an acid containing a halogen, such as hydrochloric acid, is used as the inorganic acid, the halogen sometimes remains in the oxide layer, thereby exerting adverse influences. In this case, therefore, it is preferred to use sulfuric acid or nitric acid.

Upon application of the acid treatment onto the metallic substrate, the metal hydride is usually formed at the same time on the surface of the metallic substrate. If the metal hydride is heated to about 400° to 700° C. in an oxidizing atmosphere such as air, the corresponding oxide layer can be obtained. The thickness of the metal hydride layer formed by the above acid treatment reaches 0.1 to several tens of microns. For example, in the case of titanium or a titanium alloy, when the substrate is treated for 20 to 40 minutes in 20 to 30% boiling hydrochloric acid, a metal hydride layer having a thickness of 10 to 20 $\mu$m can be obtained. When it is treated for 4 to 8 hours in 30% oxalic acid maintained at 100° C., irregularities of the surface are increased and the surface becomes pear skin-like while at the same time a metal hydride layer having a thickness of 10 to 20 $\mu$m is obtained. The metal hydride is easily oxidized on heating, thereby forming a dense oxide layer having the same thickness. Also in the case of stainless steel or a chromium-cobalt alloy, if the substrate is treated at room temperature for 2 to 10 hours in nitric acid, there can be obtained a metal hydride layer having a thickness of 10 to 20 $\mu$m.

For the formation of the metal hydride, as well as the above acid treatment, there can be employed a method in which metal hydride is formed electrolytically by passing electricity with the metallic substrate as a cathode. This method is particularly effective when the substrate is made of titanium or a titanium alloy. For example, when the substrate is treated for about 5 hours in a 15% aqueous sulfuric acid solution at 60° C., there can be obtained at a metal hydride coating having a thickness of 0.5 to 10 $\mu$m. On heating the hydride at 400° to 700° C. in the case of titanium or a titanium alloy, or at 400° to 900° C. in the case of other metal, the surface is converted into the corresponding stable oxide.

In accordance with a second embodiment of the invention, the metallic substrate is electrolytically oxidized to form an oxide or mixed oxide layer on the surface thereof. In general, when a current is passed through an electrically conductive electrolyte with titanium or a titanium alloy or a corrosion resistant metal alloy such as stainless steel as an anode, a thin layer of oxide in the passive state is formed and the voltage rises, and thus the oxide reaches the super passive state, thereby releasing oxygen. The thickness of the thin layer of oxide until the above voltage is reached is several angstromes to several hundred angstromes, which is effective for the object of the present invention. It is preferred that the thickness of the oxide layer be larger. A thick oxide layer can be formed by breaking the above passive state oxide layer at a high voltage by passing not less than 1 A/dm$^2$, preferably not less than 5 A/dm$^2$ of current. Conditions necessary for forming the oxide layer vary with, for example, the type of the metallic substrate or the electrolyte. For example, with an electrolyte containing sulfuric acid, carbonates (e.g., sodium carbonate, potassium carbonate and calcium carbonate), and/or sulfates (e.g., sodium sulfate, potassium sulfate and calcium sulfate), an oxide layer having the desired thickness can be obtained by treating for 10 seconds to 2 minutes at a voltage of 40 to 200 V and a current density of 5 to 200 A/dm$^2$. At this time, flash is sometimes generated in the electrolyte. This phenomenon is called "in-liquid flash discharge".

At the time of passing electricity, there will occur a phenomenon that the surface of the metallic substrate is partially dissolved in the electrolyte and is again deposited in the form of an oxide on the surface of the metallic substrate. If metal ions are present in the electrolyte, the metal component of the metallic substrate is deposited along with the metal ions, resulting in the formation of a layer of mixed oxide of the metal component of the metallic substrate and the metal in the electrolyte. For example, when a titanium substrate is used as the metallic substrate and oxidized in an aqueous chromium sulfate solution with the distance between electrodes as 30 mm, a current density of 100 A/dm$^2$ is obtained at a voltage of about 40 V, and in a time of 30 seconds to 1 minute, there can be obtained a mixed oxide layer of titanium oxide impregnated with chromium and having a thickness of 0.1 micron to several ten microns.

The oxide or mixed oxide layer is formed on the entire surface of the metallic surface, and the surface of the oxide or mixed oxide layer has irregularities. These irregularities are effective in forming the calcium phosphate compound layer as described hereinafter because they increase the substantial contact area and produce improved bonding properties. The oxide or mixed oxide layer is relatively large in thickness, is low in crystallinity, and in some cases, contains part of the electrolyte component. If desired, therefore, the oxide or mixed oxide layer can be stabilized by heating. Heating is suitable to be carried out in air at 200° to 700° C. Heating time can be determined appropriately, but is suitably from 10 minutes to 3 hours. If the heating temperature is less than 200° C., the OH group which may be incorporated in the oxide layer cannot be separated. On the other hand, if it is more than 700° C., the metallic substrate itself is oxidized and even if the oxide layer is stabilized, the oxide layer is easily separated from the metallic substrate.

When the metallic substrate is made of stainless steel or a cobalt-chromium alloy, unlike the case wherein the metallic substrate is made of titanium or a titanium alloy, it is necessary to pay attention to the electrolyte. That is, if anode polarization is carried out in an acidic solution, the metal surface is dissolved and the desired oxide layer becomes difficult to obtain. In a strongly alkaline solution, the oxide on the surface of the metallic substrate is partially dissolved and thus, in some cases, a sufficiently grown oxide layer cannot be obtained. Therefore, it is necessary to choose an electrolyte having a pH of 6 to 13. Although the type of the electrolyte is not critical, an aqueous solution of the carbonate or sulfate of various metals, or an organic bath containing these as the electrolyte is effectively used. Organic compounds to be used in the organic bath include ethyl alcohol, n-butyl alcohol and isopropyl alcohol.

The oxide or mixed oxide layer can be formed similarly even with an electrolyte containing halogen ions such as chlorine ions. However, even if the heat treatment is applied, the halogen ions sometimes remain in the layer. Thus, during long term use, stainless steel or a cobalt-chromium alloy is sometimes corroded, thereby producing a problem of stability. Therefore, when stainless steel or a cobalt-chromium alloy is used as the metallic substrate, it is not preferred to use an electrolyte containing a halogen.

The stainless steel and cobalt-chromium alloy has low rates of formation of the oxide layer and can withstand heating at 800° C. or above.

Even when metals or alloys other than the above described metals or alloys are used as the metallic substrate, the desired oxide layer can be obtained by appropriately determining conditions depending on the characteristics of the metal.

After the oxide or mixed oxide layer is formed on the surface of the metallic substrate, a calcium phosphate compound coating is formed on the oxide or mixed oxide layer. The calcium phosphate compound as used herein means mainly apatite hydroxide, and further includes tricalcium phosphate, calcium hydrogenphosphate and calcium dihydrogenphosphate which are all considered to be by-produced by heating or calcination of apatite hydroxide, and calcium phosphate-based compounds formed from apatite hydroxide and impurities or components of the oxide or mixed oxide layer.

The method of forming the calcium phosphate compound coating and its conditions are not critical. Typical methods are the plasma spray coating method and the thermal decomposition method.

The plasma spray coating method has an advantage of being able to easily form the coating although it suffers from disadvantages in that it needs expensive apatite hydroxide and the yield is not sufficiently high. When spray coating is applied directly onto the metal, it should be carried out under severe conditions in order to obtain satisfactory bonding properties, and such severe conditions cause partial decomposition of the expensive apatite hydroxide. In the present invention, on the other hand, the calcium phosphate compound coating is formed on the oxide layer and sufficiently satisfactory bonding properties can be obtained even if spray coating is applied under such conditions as not to cause decomposition of apatite hydroxide.

It suffices that the spray coating is carried out in an atmosphere comprising argon gas and hydrogen, and the electric power is about 30 kW. The particle diameter of the apatite hydroxide is preferably intermediate in size, for example, from about 125 to 345 mesh.

In the case of the thermal decomposition method, a nitric acid aqueous solution in which a calcium phosphate compound, preferably apatite hydroxide is dissolved and preferably saturated is coated on the surface of the oxide layer and then calcined to form a coating layer having good bonding properties to the oxide layer on the metallic substrate. In this case, the calcination product is mainly a calcium phosphate compound comprising apatite hydroxide. The optimum calcination conditions vary with the solution to be used, particularly the nitric acid concentration. As the nitric acid concentration is increased, the optimum temperature is increased. The optimum temperature is 350° to 500° C. at 10% nitric acid and 450° to 800° C. at 60% nitric acid. The calcination temperature is preferably in the range of 300° to 800° C. If the calcination temperature is less than 300° C., the strength of the calcium phosphate compound coating is insufficiently low. On the other hand, if it is more than 800° C., the rate of oxidation of the metallic substrate is increased and separation of the oxide layer from the metallic substrate easily occurs. Although the calcination can be carried out in an oxidizing atmosphere exemplified by air, it is preferred to be carried out in an inert atmosphere exemplified by argon.

The coating layer can also be formed by coating a solution of a mixture of calcium carbonate and calcium phosphate in a suitable ratio and then calcinating in an oxidizing or inert atmosphere. In this case, it is preferred that hydrothermal treatment be applied to increase crystallinity.

In accordance with the above procedures, there can be obtained an implant material which is good in workability, is sufficiently high in mechanical strength, has increased affinity in the bone tissue and living body, and can hold stable bonding properties to the living body over a long time.

The present invention is described in greater detail with reference to the following examples although it is not intended to be limited thereto.

Unless otherwise specified, all ratios, percents, etc. are by weight.

EXAMPLE 1

A 40 mm×20 mm piece of stainless steel was cut out of a SUS 316L rolled sheet having a thickness of 1 mm. The surface of the piece was made coarse by applying blast treatment with a #80 steel shot. This piece was used as a metallic substrate. This metallic substrate was degreased with trichloroethylene vapor and then soaked in a 25 wt % aqueous nitric acid solution at room temperature for 30 minutes to remove surface attachments such as blast sand residue.

The stainless steel substrate thus rinsed was coated with a 30% aqueous nitric acid solution, dried by allowing to stand at room temperature, placed in a muffle furnace maintained at 600° C. through which air was passed, and oxidized by heating for 15 minutes. On repeating this procedure three times, a stainless steel substrate with a blue oxide layer having a thickness of about 5 μm was obtained.

Tape testing showed that the oxide layer was firmly bonded to the metallic substrate.

On the oxide layer thus formed was formed a calcium phosphate compound coating composed mainly of apatite hydroxide by the method as described below.

3 g of apatite hydroxide powder was dissolved in 10 g of a 25% aqueous nitric acid solution to prepare a coating solution. This coating solution was coated on the oxide layer of the metallic substrate and thermally decomposed at 500° C. for 10 minutes in a muffle furnace while flowing argon therethrough to obtain the calcium phosphate compound coating. In addition, the coating-heating operation was repeated three times.

The calcium phosphate compound coating thus formed was made substantially of apatite hydroxide and firmly bonded to the metallic surface through the oxide layer.

EXAMPLE 2

A 40 mm×20 mm piece was cut out of a JIS No. 1 titanium rolled sheet having a thickness of 1 mm and was subjected to the same pre-treatment as in Example 1 to prepare a metallic substrate.

This titanium substrate was soaked in a 30 wt % aqueous sulfuric acid solution maintained at 95° C. for 15 minutes. During this soaking, hydrogen was vigorously generated simultaneously with dissolution of titanium. The titanium substrate was taken out of the solution, placed as it was in a muffle furnace maintained at 550° C., and kept therein for 20 minutes. By this operation, a blue and strong titanium oxide layer was formed. The titanium substrate covered with titanium oxide was coated with apatite hydroxide powder adjusted in particle diameter to 125 to 345 mesh, by the plasma spray coating method.

The plasma spray coating method was carried out under the following conditions: plasma gas ($Ar/H_2=5/1$ by volume); arc voltage: 60 V; arc current: 500 Å.

By this spray coating, a strong coating of apatite hydroxide containing tricalcium phosphate was formed.

EXAMPLE 3

A metallic substrate was produced from a JIS No. 1 titanium rolled sheet having a thickness of 1 mm in the same manner as in Example 1. Electrolysis was carried out in a 20% aqueous hydrochloric acid solution at 60° C. at a current density of 100 $A/dm^2$ with the above titanium substrate as the cathode. By this operation, the surface of the titanium substrate become grey-white. An X-ray diffraction analysis showed that $TiH_2$ was formed on the surface of the titanium substrate.

The titanium substrate was heated at 450° C. for 30 minutes in a muffle furnace through which a mixed gas of 25 vol % of oxygen atom and 75 vol % of nitrogen was passed. At the end of the time, the surface of the metallic substrate became yellow-brown. An X-ray diffraction analysis showed that a rutile type oxide was formed on the surface of the titanium substrate.

On the titanium substrate with the surface oxide layer formed thereon was formed an apatite hydroxide layer under the same conditions as in Example 1. The apatite hydroxide layer was firmly bonded, and no peeling was observed in the tape testing.

EXAMPLE 4

A 40 mm×20 mm piece was cut out of a JIS No. 1 titanium rolled sheet having a thickness of 1 mm and then degreased in trichloroethylene vapor to prepare a metallic substrate. Electrolysis was carried out with the above metallic substrate as an anode and a 5% aqueous potassium carbonate solution as an electrolyte. When the current density was raised to 50 $A/dm^2$, flash was generated in the solution and the titanium substrate was partially dissolved, making the solution turbid. At this time, the voltage was 70 V. Electricity was passed for 1 minute. At the end of the time, the titanium substrate was taken out and it was found that the surface of the titanium substrate was pear shin-like and covered with a white, hard coating. The titanium substrate was rinsed with deionized water and then dried. The white coating on the surface was identified by the use of an X-ray diffractometer and found to be rutile (TiO$_2$) having a low degree of crystallinity.

On the surface of the titanium substrate with the oxide layer formed thereon was formed a coating made mainly of apatite hydroxide by the thermal decomposition method. That is, 3 g of apatite hydroxide powder was dissolved in 10 g of a 25% aqueous nitric acid solution to prepare a coating solution for formation of the coating. This coating solution was coated on the above oxide layer and was subjected to thermal decomposition in an argon gas atmosphere at 500° C. for 15 minutes. This coating-heating operation was further repeated four times. Thus a very strong coating made substantially of apatite hydroxide was formed on the titanium substrate through the oxide layer of titanium oxide.

EXAMPLE 5

A titanium substrate was prepared in the same manner as in Example 4. Electrolysis was carried out with the titanium substrate as anode and an aqueous solution of a mixture of 50 g/l of cobalt sulfate and 50 g/l of sulfuric acid as an electrolyte. When the current density was increased to 100 A/dm$^2$, flash was generated in the solution and the titanium substrate was partially dissolved, making the solution turbid. The voltage at this time was 50 V. After electricity was passed for 1 minute, the titanium substrate was taken out of the solution. The surface of the titanium substrate was pear skin-like and covered with a yellow-green hard coating. The titanium substrate was rinsed with deionized water and dried, and then place in an electric furnace through which air was flowed, maintained at 500° C. and heated for 1 hour. No change in color due to this heating was observed.

In order to examine the constitutional component and structure of the mixed oxide layer above obtained, an elemental analysis was carried out by the use of an X-ray microanalyzer and also an analysis using an X-ray diffractometer was carried out. The elemental analysis showed that the constitutional component was Ti/Co=95/5 (metal mol %). The X-ray diffraction analysis showed that the oxide layer was of a rutile type crystal phase and was a solid solution of Co in a rutile type titanium oxide (TiO$_2$).

On this titanium substrate was formed a coating of apatite hydroxide under the same conditions as in Example 4. The bonding strength of the coating to the titanium substrate was measured by the tape testing. No separation of the coating was observed at all.

EXAMPLE 6

A 40 mm×20 mm piece was cut out of a stainless steel SUS 316L sheet having a thickness of 1 mm, and its surface was made coarse by applying blast treatment with a #80 steel shot. This SUS 316L piece was soaked in a 25% aqueous hydrochloric acid solution at 40° C. for 30 minutes to remove surface attachment.

With the above stainless steel substrate as the anode, electrolysis was carried out in a 0.5 mol % aqueous calcium carbonate carbonate solution adjusted to pH 12 at 95° C. First the electrolysis was carried out at a current density of 0.5 A/dm$^2$, but no oxide layer was formed on the surface. The electrolysis was continued at a current density of 1 A/dm$^2$. On continuing the electrolysis for about 30 minutes, the surface of the substrate became black and the electrolytic voltage rose by 1 V. Further the electrolysis was continued for 60 minutes. The voltage rose by 2 V. Then, since the voltage began to rise abruptly, the electrolysis was stopped. The stainless steel substrate was rinsed with deionized water, and then placed in an electric furnace maintained at 350° C. and heated for 1 hour. Examination of the surface of the substrate by the X-ray diffraction method showed that the surface was made of an oxide comprising mainly $\alpha$-Fe$_2$O$_3$ of low crystallinity.

On the above stainless steel substrate was formed a calcium phosphate compound coating made mainly of apatite hydroxide by the plasma spray coating method. On spray coating a reagent grade of apatite hydroxide power having a particle size of 125 to 345 mesh having a plasma gas of argon and hydrogen (volume ratio: 5/1) at an arc voltage of 60 V and an arc current of 500 A, a coating having a thickness of about 100 $\mu$m was formed. This coating was apatite hydroxide containing a very small amount of tricalcium phosphate. The coating caused no separation in the tape testing, and it was found that the coating had great bonding properties.

Some of the advantages of the present invention are described below.

(1) Since metals, especially corrosion resistant metals such as titanium, titanium alloys, stainless steel and chromium-cobalt alloys are used as the metallic substrate and a layer of the oxide of metal including the metal component of the metallic substrate is formed on the surface of the metallic substrate by either heating or electrolytic oxidation, the composite material of the present invention, when used as an artificial bone or artificial tooth root, is harmless to the living body, is stable, is almost free of the possibility of dissolution, and further is sufficiently high in mechanical strength and is easy to work.

(2) Since the surface of the metallic substrate is covered with a calcium phosphate compound exemplified by apatite hydroxide, the composite material of the present invention exhibits sufficiently high affinity in the living body and thus can be bonded to the bone in the living body with ease and further with high strength.

(3) Since, as described above, the metal oxide layer is formed on the surface of the metallic substrate, even when the calcium phosphate compound particularly excellent in affinity is absorbed in the bone tissue over a long time after implantation in the living body, the oxide layer formed on the metallic substrate prevents the metallic substrate from coming into direct contact with the bone tissue and also prevents degradation of bonding properties between them as based on insufficient affinity between the bone tissue and the metallic substrate. Thus the calcium phosphate compound-coated composite material of the present invention can be used as an implant material without causing any change in the stability thereof for a long time.

(4) Since the metal oxide layer is formed between the calcium phosphate coating and the metallic substrate and the coating can be firmly bonded on the metal oxide layer by plasma spray coating even under relatively mild conditions, the coating layer can be formed easily and it becomes possible to employ the spray coating method which has not been employed because of decomposition of apatite hydroxide.

While the invention has been described in detail and with reference to specific embodiments thereof, it will be apparent to one skilled in the art that various changes and modifications can be made therein without departing from the spirit and scope thereof.

What is claimed is:

1. A process for producing a calcium phosphate compound-coated composite material which comprises oxidizing a metallic substrate to form a layer of an oxide of the metal component of the substrate on the surface of the substrate, and forming a coating layer of a calcium phosphate compound on the surface of the oxide layer.

2. The process as claimed in claim 1, wherein the metallic substrate is made of a corrosion resistant metal or alloy selected from the group consisting of titanium, titanium alloys, stainless steel and cobalt-chromium base alloys.

3. The process as claimed in claim 1, wherein the layer of the oxide of the metal component is formed by heat-oxidizing the metallic substrate.

4. The process as claimed in claim 3, wherein the surface of the metallic substrate is previously subjected to acid treatment to convert the metallic substrate surface into metal hydride and then the surface is heat-oxidized.

5. The process as claimed in claim 3, wherein the surface of the metallic substrate is previously converted into metal hydride by passing electricity in an electrolyte with the metallic substrate as a cathode, and then the surface is heat-oxidized.

6. The process as claimed in claim 1, wherein the metallic substrate is electrolytically oxidized in an electrically conductive electrolyte with the metallic substrate as an anode to form a layer of the oxide of the metallic substrate component alone or a layer of a mixed oxide of the metallic substrate component and a metal component of the electrolyte.

7. The process as claimed in claim 6, wherein the metallic substrate is titanium or a titanium alloy and is electrolyzed in an electrolyte containing sulfuric acid, a sulfate and/or a carbonate at a current density of not less than 1 $A/dm^2$ to form the oxide or mixed oxide layer on the surface of the metallic substrate.

8. The process as claimed in claim 6, wherein the metallic substrate is titanium and is electrolyzed in an electrolyte containing cobalt and/or chromium ion at a current density of not less than 1 $A/dm^2$ to form a mixed oxide layer containing cobalt and/or chromium on the surface of the metallic substrate.

9. The process as claimed in claim 6, wherein the metallic substrate is stainless steel or a chromium-cobalt base alloy and is electrolyzed in a neutral or weak alkaline aqueous solution or an organic solution as an electrolyte as a current density of not less than 1 $A/dm^2$ to form an oxide layer on the surface of the metallic substrate.

10. The process as claimed in claim 6, wherein the metallic substrate is stainless steel or a chromium-cobalt base alloy and is electrolyzed in an electrolyte containing cobalt and/or chromium at a current density of not less than 1 $A/dm^2$ to form a mixed oxide layer containing cobalt and/or chromium.

11. The process as claimed in claim 6, wherein the metallic substrate with the oxide layer formed thereon is heated in air at 200° to 700° C., and then a coating of a calcium phosphate compound is formed.

* * * * *